United States Patent
Vijayakumar

(10) Patent No.: US 9,453,938 B2
(45) Date of Patent: Sep. 27, 2016

(54) LASER SPECTROSCOPY FOR DOWNHOLE SENSING OF GASES AND FLUIDS

(71) Applicant: Schlumberger Technology Corporation, Sugar Land, TX (US)

(72) Inventor: Arjun Vijayakumar, Sugar Land, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 14/574,317

(22) Filed: Dec. 17, 2014

(65) Prior Publication Data
US 2016/0178793 A1  Jun. 23, 2016

(51) Int. Cl.
*G01V 8/02* (2006.01)
*G01N 21/3577* (2014.01)

(52) U.S. Cl.
CPC ............. *G01V 8/02* (2013.01); *G01N 21/3577* (2013.01); *G01N 2201/0612* (2013.01)

(58) Field of Classification Search
CPC ............... G01V 8/02; G01N 21/3577; G01N 2201/0612
See application file for complete search history.

(56) References Cited

U.S. PATENT DOCUMENTS 8,068,226 B2   11/2011   Csutak
2009/0180101 A1*  7/2009  Csutak .......... G01N 21/51 356/70
2013/0118734 A1*  5/2013  Csutak .......... E21B 49/10 166/264
2015/0357794 A1* 12/2015  Tsuji ............ H01S 5/3402 372/45.012

FOREIGN PATENT DOCUMENTS

WO   2006063094 A1   6/2006
WO   2012094007 A2   7/2012

OTHER PUBLICATIONS

Fujisawa, et al. "Development and Applications of Ruggedized VIS/NIR Spectrometer System for Oilfield Wellbores," Photonic Sensors (2013) vol. 3, No. 4: pp. 289-294.
Salisbury, et al. "Thermal Infrared Remote Sensing of Crude Oil Slicks," Remote Sens. Environ. (1993) 45: pp. 225-231.

* cited by examiner

*Primary Examiner* — Christine Sung
(74) *Attorney, Agent, or Firm* — David G. Matthews; Cathy Hewitt

(57) ABSTRACT

A method for spectroscopic analysis of a fluid using electromagnetic radiation from lasers is provided. In one embodiment, the method includes sampling formation fluid within a well and determining formation fluid properties for the sampled formation fluid through downhole fluid analysis. Determining formation fluid properties for the sampled formation fluid can include using a spectrometer having a plurality of quantum cascade lasers to determine optical properties of the formation fluid and determining levels of multiple chemical species in the formation fluid using the determined optical properties of the formation fluid. Various other methods, systems and devices are also disclosed.

8 Claims, 7 Drawing Sheets

LASER SPECTROSCOPY FOR DOWNHOLE SENSING OF GASES AND FLUIDS

BACKGROUND

Wells are generally drilled into subsurface rocks to access fluids, such as hydrocarbons, stored in subterranean formations. The formations penetrated by a well can be evaluated for various purposes, including for identifying hydrocarbon reservoirs within the formations. During drilling operations, one or more drilling tools in a drill string may be used to test or sample the formations. Following removal of the drill string, a wireline tool may also be run into the well to test or sample the formations. These drilling tools and wireline tools, as well as other wellbore tools conveyed on coiled tubing, drill pipe, casing or other means of conveyance, are also referred to herein as "downhole tools." Certain downhole tools may include two or more integrated collar assemblies, each for performing a separate function, and a downhole tool may be employed alone or in combination with other downhole tools in a downhole tool string.

Formation evaluation may involve drawing fluid from the formation into a downhole tool. In some instances, the fluid drawn from the formation is retained within the downhole tool for later testing outside of the well. In other instances, downhole fluid analysis may be used to test the fluid while it remains in the well. Such analysis can be used to provide information on certain fluid properties in real time without the delay associated with returning fluid samples to the surface.

SUMMARY

Certain aspects of some embodiments disclosed herein are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

In one embodiment of the present disclosure, a method includes sampling formation fluid and determining properties of the sampled formation fluid through downhole fluid analysis. Determining properties of the sample formation fluid includes using a spectrometer having quantum cascade lasers to determine optical properties of the formation fluid and determining levels of multiple chemical species in the formation fluid using the determined optical properties of the formation fluid.

In another embodiment, a method includes receiving a fluid in a spectrometer having an emitter with multiple quantum cascade lasers fabricated on a shared semiconductor substrate. The method also includes using the multiple quantum lasers to irradiate the received fluid with mid-infrared radiation at different energy levels and detecting portions of the radiation transmitted through the received fluid. Multiple chemical species within the received fluid can then be identified based on the detected portions of the mid-infrared radiation.

In a further embodiment, an apparatus includes a downhole tool having an intake for receiving formation fluid within the downhole tool. The downhole tool also includes a spectrometer with a laser for emitting electromagnetic energy within the mid-infrared portion of the electromagnetic spectrum and a detector positioned to receive the electromagnetic energy transmitted from the laser through the formation fluid. Further, the apparatus includes a controller for identifying chemical species in the formation fluid based on optical data for the formation fluid acquired with the spectrometer in the mid-infrared portion of the electromagnetic spectrum.

Various refinements of the features noted above may exist in relation to various aspects of the present embodiments. Further features may also be incorporated in these various aspects as well. These refinements and additional features may exist individually or in any combination. For instance, various features discussed below in relation to the illustrated embodiments may be incorporated into any of the above-described aspects of the present disclosure alone or in any combination. Again, the brief summary presented above is intended just to familiarize the reader with certain aspects and contexts of some embodiments without limitation to the claimed subject matter.

BRIEF DESCRIPTION OF THE DRAWINGS

The present disclosure is understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION OF SPECIFIC EMBODIMENTS

It is to be understood that the present disclosure provides many different embodiments, or examples, for implementing different features of various embodiments. Specific examples of components and arrangements are described below for purposes of explanation and to simplify the present disclosure. These are, of course, merely examples and are not intended to be limiting.

When introducing elements of various embodiments, the articles "a," "an," "the," and "said" are intended to mean that there are one or more of the elements. The terms "comprising," "including," and "having" are intended to be inclusive and mean that there may be additional elements other than the listed elements. Moreover, any use of "top," "bottom," "above," "below," other directional terms, and variations of these terms is made for convenience, but does not mandate any particular orientation of the components.

The present disclosure relates to detection of chemical species in a fluid via laser spectroscopy. More particularly, some embodiments relate to downhole fluid analysis and detection of chemical species using laser spectroscopy in the mid-infrared region of the electromagnetic spectrum. In some instances, such analysis can be used downhole in real time to detect gases and other fluids, such as levels of carbon dioxide, hydrogen sulfide, methane, ethane, and several other crude oil species. Further, at least some embodiments include using a spectrometer having an emitter with at least one quantum cascade laser as a mid-infrared source for analyzing fluids and identifying species.

Figure 1:
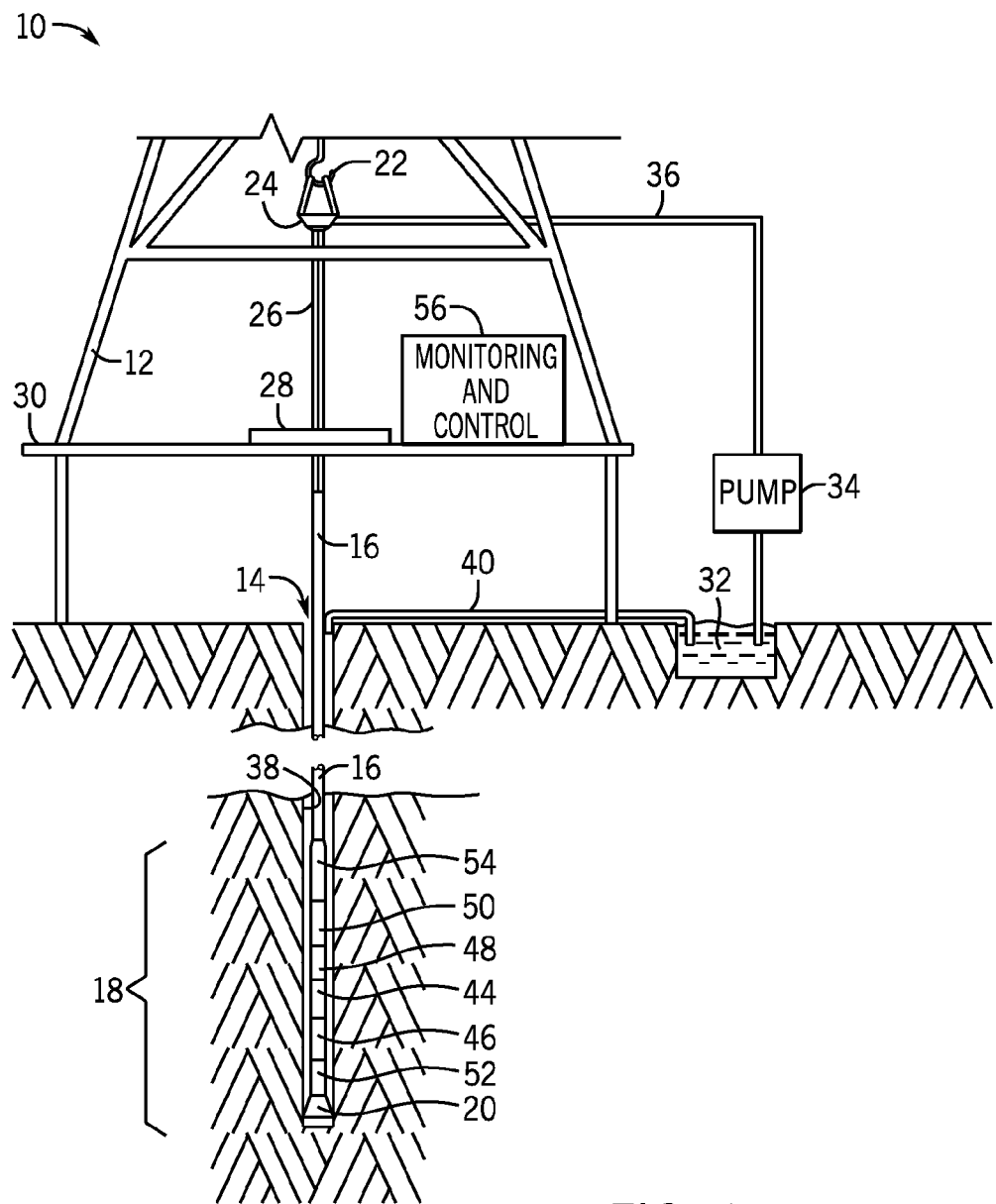
FIG. 1 generally depicts a drilling system having a fluid sampling tool in a drill string in accordance with one embodiment of the present disclosure.

Turning now to the drawings, a drilling system 10 is depicted in FIG. 1 in accordance with one embodiment. While certain elements of the drilling system 10 are depicted in this figure and generally discussed below, it will be appreciated that the drilling system 10 may include other components in addition to, or in place of, those presently illustrated and discussed. As depicted, the system 10 includes a drilling rig 12 positioned over a well 14. Although depicted as an onshore drilling system 10, it is noted that the drilling system could instead be an offshore drilling system. The drilling rig 12 supports a drill string 16 that includes a bottomhole assembly 18 having a drill bit 20. The drilling rig 12 can rotate the drill string 16 (and its drill bit 20) to drill the well 14.

The drill string 16 is suspended within the well 14 from a hook 22 of the drilling rig 12 via a swivel 24 and a kelly 26. Although not depicted in FIG. 1, the skilled artisan will appreciate that the hook 22 can be connected to a hoisting system used to raise and lower the drill string 16 within the well 14. As one example, such a hoisting system could include a crown block and a drawworks that cooperate to raise and lower a traveling block (to which the hook 22 is connected) via a hoisting line. The kelly 26 is coupled to the drill string 16, and the swivel 24 allows the kelly 26 and the drill string 16 to rotate with respect to the hook 22. In the presently illustrated embodiment, a rotary table 28 on a drill floor 30 of the drilling rig 12 is constructed to grip and turn the kelly 26 to drive rotation of the drill string 16 to drill the well 14. In other embodiments, however, a top drive system could instead be used to drive rotation of the drill string 16.

During operation, drill cuttings or other debris may collect near the bottom of the well 14. Drilling fluid 32, also referred to as drilling mud, can be circulated through the well 14 to remove this debris. The drilling fluid 32 may also clean and cool the drill bit 20 and provide positive pressure within the well 14 to inhibit formation fluids from entering the wellbore. In FIG. 1, the drilling fluid 32 is circulated through the well 14 by a pump 34. The drilling fluid 32 is pumped from a mud pit (or some other reservoir, such as a mud tank) into the drill string 16 through a supply conduit 36, the swivel 24, and the kelly 26. The drilling fluid 32 exits near the bottom of the drill string 16 (e.g., at the drill bit 20) and returns to the surface through the annulus 38 between the wellbore and the drill string 16. A return conduit 40 transmits the returning drilling fluid 32 away from the well 14. In some embodiments, the returning drilling fluid 32 is cleansed (e.g., via one or more shale shakers, desanders, or desilters) and reused in the well 14.

In addition to the drill bit 20, the bottomhole assembly 18 also includes various instruments that measure information of interest within the well 14. For example, as depicted in FIG. 1, the bottomhole assembly 18 includes a logging-while-drilling (LWD) module 44 and a measurement-while-drilling (MWD) module 46. Both modules include sensors, housed in drill collars, that collect data and enable the creation of measurement logs in real-time during a drilling operation. The modules could also include memory devices for storing the measured data. The LWD module 44 includes sensors that measure various characteristics of the rock and formation fluid properties within the well 14. Data collected by the LWD module 44 could include measurements of gamma rays, resistivity, neutron porosity, formation density, sound waves, optical density, and the like. The MWD module 46 includes sensors that measure various characteristics of the bottomhole assembly 18 and the wellbore, such as orientation (azimuth and inclination) of the drill bit 20, torque, shock and vibration, the weight on the drill bit 20, and downhole temperature and pressure. The data collected by the MWD module 46 can be used to control drilling operations. The bottomhole assembly 18 can also include one or more additional modules 48, which could be LWD modules, MWD modules, or some other modules. It is noted that the bottomhole assembly 18 is modular, and that the positions and presence of particular modules of the assembly could be changed as desired. Further, as discussed in greater detail below, one or more of the modules 44, 46, and 48 could include a fluid sampling tool configured to obtain a sample of a fluid from a subterranean formation and perform downhole fluid analysis to measure properties (e.g., contamination and optical densities) of the sampled fluid.

The bottomhole assembly 18 can also include other modules. As depicted in FIG. 1 by way of example, such other modules include a power module 50, a steering module 52, and a communication module 54. In one embodiment, the power module 50 includes a generator (such as a turbine) driven by flow of drilling mud through the drill string 16. In other embodiments the power module 50 could also or instead include other forms of power storage or generation, such as batteries or fuel cells. The steering module 52 may include a rotary-steerable system that facilitates directional drilling of the well 14. The communication module 54 enables communication of data (e.g., data collected by the LWD module 44 and the MWD module 46) between the bottomhole assembly 18 and the surface. In one embodiment, the communication module 54 communicates via mud pulse telemetry, in which the communication module 54 uses the drilling fluid 32 in the drill string as a propagation medium for a pressure wave encoding the data to be transmitted.

The drilling system 10 also includes a monitoring and control system 56. The monitoring and control system 56 can include one or more computer systems that enable monitoring and control of various components of the drilling system 10. The monitoring and control system 56 can also receive data from the bottomhole assembly 18 (e.g., data from the LWD module 44, the MWD module 46, and the additional module 48) for processing and for communication to an operator, to name just two examples. While depicted on the drill floor 30 in FIG. 1, it is noted that the monitoring and control system 56 could be positioned elsewhere, and that the system 56 could be a distributed system with elements provided at different places near or remote from the well 14.

Figure 2:
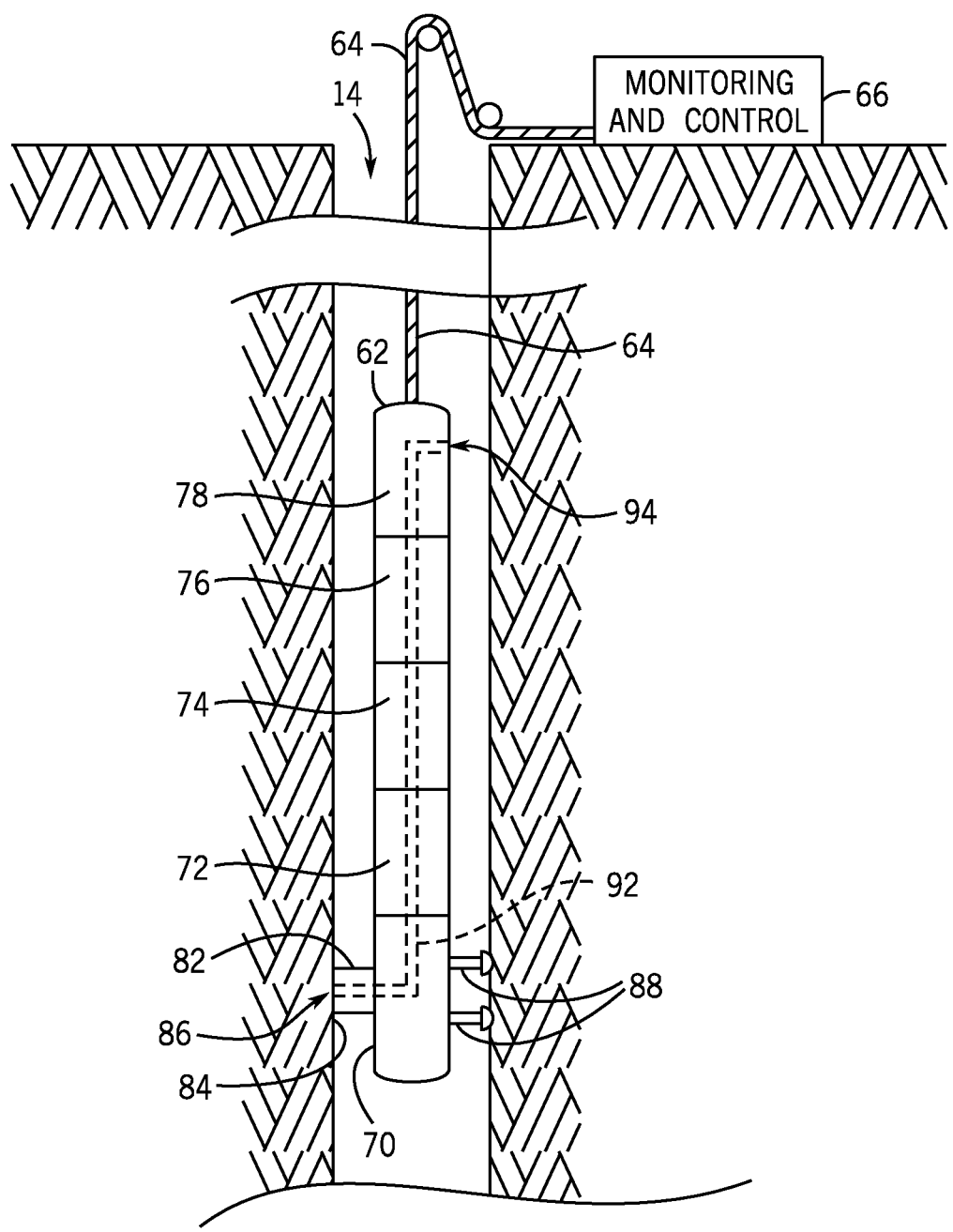
FIG. 2 generally depicts a fluid sampling tool deployed within a well on a wireline in accordance with one embodiment.

Another example of using a downhole tool for formation testing within the well 14 is depicted in FIG. 2. In this embodiment, a fluid sampling tool 62 is suspended in the well 14 on a cable 64. The cable 64 may be a wireline cable with at least one conductor that enables data transmission between the fluid sampling tool 62 and a monitoring and control system 66. The cable 64 may be raised and lowered within the well 14 in any suitable manner. For instance, the cable 64 can be reeled from a drum in a service truck, which may be a logging truck having the monitoring and control system 66. The monitoring and control system 66 controls movement of the fluid sampling tool 62 within the well 14 and receives data from the fluid sampling tool 62. In a similar fashion to the monitoring and control system 56 of FIG. 1, the monitoring and control system 66 may include one or more computer systems or devices and may be a distributed computing system. The received data can be stored, communicated to an operator, or processed, for instance. While the fluid sampling tool 62 is here depicted as being deployed by way of a wireline, in some embodiments the fluid sampling tool 62 (or at least its functionality) is incorporated into or as one or more modules of the bottom-hole assembly 18, such as the LWD module 44 or the additional module 48.

The fluid sampling tool 62 can take various forms. While it is depicted in FIG. 2 as having a body including a probe module 70, a fluid analysis module 72, a pump module 74, a power module 76, and a fluid storage module 78, the fluid sampling tool 62 may include different modules in other embodiments. The probe module 70 includes a probe 82 that may be extended (e.g., hydraulically driven) and pressed into engagement against a wall 84 of the well 14 to draw fluid from a formation into the fluid sampling tool 62 through an intake 86. As depicted, the probe module 70 also includes one or more setting pistons 88 that may be extended outwardly to engage the wall 84 and push the end face of the probe 82 against another portion of the wall 84. In some embodiments, the probe 82 includes a sealing element or packer that isolates the intake 86 from the rest of the wellbore. In other embodiments the fluid sampling tool 62 could include one or more inflatable packers that can be extended from the body of the fluid sampling tool 62 to circumferentially engage the wall 84 and isolate a region of the well 14 near the intake 86 from the rest of the wellbore. In such embodiments, the extendable probe 82 and setting pistons 88 could be omitted and the intake 86 could be provided in the body of the fluid sampling tool 62, such as in the body of a packer module housing an extendable packer.

The pump module 74 draws the sampled formation fluid into the intake 86, through a flowline 92, and then either out into the wellbore through an outlet 94 or into a storage container (e.g., a bottle within fluid storage module 78) for transport back to the surface when the fluid sampling tool 62 is removed from the well 14. The fluid analysis module 72, which may also be referred to as the fluid analyzer 72, includes one or more sensors for measuring properties of the sampled formation fluid, such as the optical density of the fluid, and the power module 76 provides power to electronic components of the fluid sampling tool 62.

The drilling and wireline environments depicted in FIGS. 1 and 2 are examples of environments in which a fluid sampling tool may be used to facilitate analysis of a downhole fluid. The presently disclosed techniques, however, could be implemented in other environments as well. For instance, the fluid sampling tool 62 may be deployed in other manners, such as by a slickline, coiled tubing, or a pipe string.

Figure 3:
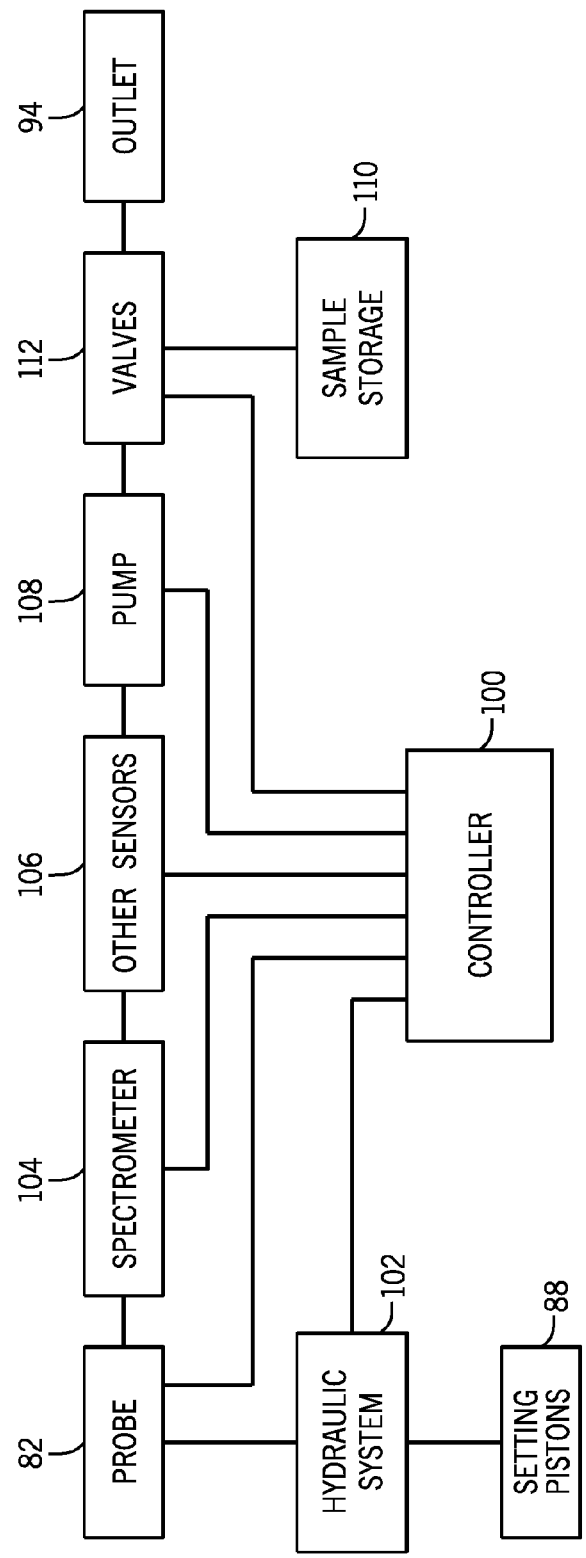
FIG. 3 is a block diagram of components of a fluid sampling tool operated by a controller in accordance with one embodiment.

Additional details as to the construction and operation of the fluid sampling tool 62 may be better understood through reference to FIG. 3. As shown in this figure, various components for carrying out functions of the fluid sampling tool 62 are connected to a controller 100. The various components include a hydraulic system 102 connected to the probe 82 and the setting pistons 88, a spectrometer 104 for measuring fluid optical properties, one or more other sensors 106, a pump 108, and valves 112 for diverting sampled fluid into storage devices 110 rather than venting it through the outlet 94.

In operation, the hydraulic system 102 extends the probe 82 and the setting pistons 88 to facilitate sampling of a formation fluid through the wall 84 of the well 14. It also retracts the probe 82 and the setting pistons 88 to facilitate subsequent movement of the fluid sampling tool 62 within the well. The spectrometer 104, which can be positioned within the fluid analyzer 72, collects data about optical properties of the sampled formation fluid. Such measured optical properties can include optical densities (absorbance) of the sampled formation fluid at different wavelengths of electromagnetic radiation. Using the optical densities, the composition of a sampled fluid (e.g., volume fractions of its constituent components) can be determined. Other sensors 106 can be provided in the fluid sampling tool 62 (e.g., as part of the probe module 70 or the fluid analyzer 72) to take additional measurements related to the sampled fluid. In various embodiments, these additional measurements could include pressure and temperature, density, viscosity, electrical resistivity, saturation pressure, and fluorescence, to name several examples. Other characteristics, such as gas—oil ratio (GOR), can also be determined using the measurements.

Any suitable pump 108 may be provided in the pump module 74 to enable formation fluid to be drawn into and pumped through the flowline 92 in the manner discussed above. Storage devices 110 for formation fluid samples can include any suitable vessels (e.g., bottles) for retaining and transporting desired samples within the fluid sampling tool 62 to the surface. Both the storage devices 110 and the valves 112 may be provided as part of the fluid storage module 78.

In the embodiment depicted in FIG. 3, the controller 100 facilitates operation of the fluid sampling tool 62 by controlling various components. Specifically, the controller 100 directs operation (e.g., by sending command signals) of the hydraulic system 102 to extend and retract the probe 82 and the setting pistons 88 and of the pump 108 to draw formation fluid samples into and through the fluid sampling tool. The controller 100 also receives data from the spectrometer 104 and the other sensors 106. This data can be stored by the controller 100 or communicated to another system (e.g., the monitoring and control system 56 or 66) for analysis. In some embodiments, the controller 100 is itself capable of analyzing the data it receives from the spectrometer 104 and the other sensors 106. The controller 100 also operates the valves 112 to divert sampled fluids from the flowline 92 into the storage devices 110.

Figure 4:
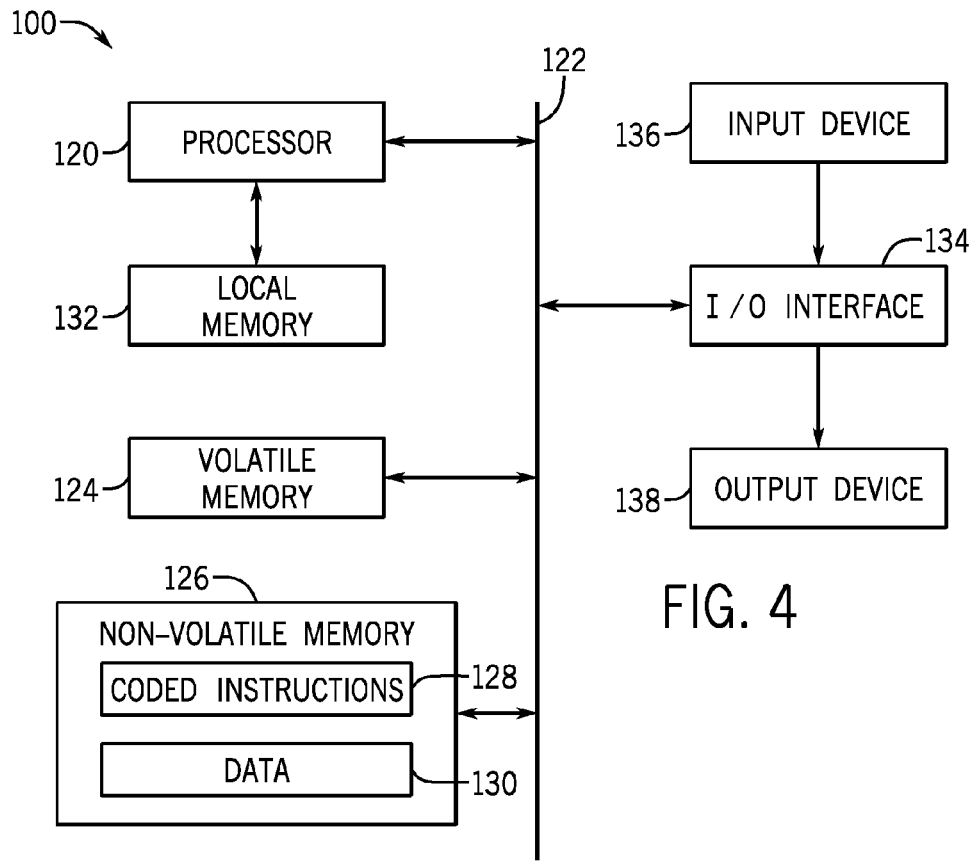
FIG. 4 is a block diagram of components in one example of the controller illustrated in FIG. 3.

The controller 100 in some embodiments is a processor-based system, an example of which is provided in FIG. 4. In this depicted embodiment, the controller 100 includes at least one processor 120 connected, by a bus 122, to volatile memory 124 (e.g., random-access memory) and non-volatile memory 126 (e.g., flash memory and a read-only memory (ROM)). Coded application instructions 128 (e.g., software that may be executed by the processor 120 to enable the control and analysis functionality described herein, including analyzing mid-infrared optical data and identifying species of interest in a sampled fluid) and data 130 are stored in the non-volatile memory 126. For example, the application instructions 128 can be stored in a ROM and the data can be stored in a flash memory. The instructions 128 and the data 130 may be also be loaded into the volatile memory 124 (or in a local memory 132 of the processor) as desired, such as to reduce latency and increase operating efficiency of the controller 100.

An interface 134 of the controller 100 enables communication between the processor 120 and various input devices 136 and output devices 138. The interface 134 can include any suitable device that enables such communication, such as a modem or a serial port. In some embodiments, the input devices 136 include one or more sensing components of the fluid sampling tool 62 (e.g., the spectrometer 104) and the output devices 138 include displays, printers, and storage devices that allow output of data received or generated by the controller 100. Input devices 136 and output devices 138 may be provided as part of the controller 100, although in other embodiments such devices may be separately provided.

The controller 100 can be provided as part of the monitoring and control systems 56 or 66 outside of a well 14 to enable downhole fluid analysis of samples obtained by the fluid sampling tool 62. In such embodiments, data collected by the fluid sampling tool 62 can be transmitted from the well 14 to the surface for analysis by the controller 100. In some other embodiments, the controller 100 is instead provided within a downhole tool in the well 14, such as within the fluid sampling tool 62 or in another component of the bottomhole assembly 18, to enable downhole fluid analysis to be performed within the well 14. Further, the controller 100 may be a distributed system with some components located in a downhole tool and others provided elsewhere (e.g., at the surface of the wellsite).

Whether provided within or outside the well 14, the controller 100 can receive data collected by the sensors within the fluid sampling tool 62 and process this data to determine one or more characteristics of the sampled fluid. Examples of such characteristics include fluid type, GOR, formation volume factor, hydrocarbon composition, carbon dioxide content, hydrogen sulfide content, asphaltene content, compressibility, saturation pressure, water content, density, viscosity, and contamination level.

Some of the data collected by the fluid sampling tool 62 relates to optical properties (e.g., optical densities) of a sampled fluid measured by the spectrometer 104. To facilitate measurements, in some embodiments the spectrometer 104 may be arranged about the flowline 92 of the fluid sampling tool 62 in the manner generally depicted in FIG. 5. In this example, the spectrometer 104 includes an emitter 142 of electromagnetic radiation, such as a light source, and a detector 144 disposed about the flowline 92 in the fluid sampling tool 62. A light source provided as the emitter 142 can be any suitable light-emitting device, such as one or more lasers, light-emitting diodes, or incandescent lamps. In at least some embodiments, the emitter 142 includes a quantum cascade laser as a light source. As used herein, the term "visible light" is intended to mean electromagnetic radiation within the visible spectrum, and the shorter term "light" is intended to include not just electromagnetic radiation within the visible spectrum, but also infrared and ultraviolet radiation.

In operation, a sampled formation fluid 146 within the flowline 92 is irradiated with electromagnetic radiation 148 (e.g., light) from the emitter 142. The electromagnetic radiation 148 includes radiation of any desired wavelengths within the electromagnetic spectrum. The electromagnetic radiation 148 could have a continuous spectrum within one or both of the visible range and the short- and near-infrared (SNIR) range of the electromagnetic spectrum, and the detector 144 could filter or diffract the received electromagnetic radiation 148. As discussed below, however, in some embodiments the electromagnetic radiation 148 is within the mid-infrared (mid-IR) portion of the electromagnetic spectrum (i.e., with wavelengths between three microns and twenty microns). The detector 144 may include a single detector or multiple detectors each assigned to separately measure light of a different wavelength.

Figure 5:
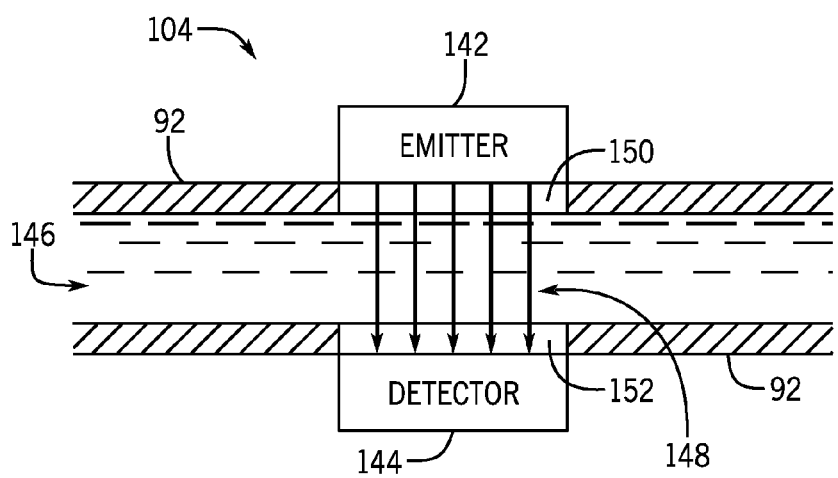
FIG. 5 generally depicts a spectrometer positioned about a flowline to enable measurement of an optical property of a fluid within the flowline in accordance with one embodiment.

As depicted in FIG. 5, the flowline 92 includes windows 150 and 152 (e.g., sapphire windows) that isolate the emitter 142 and the detector 144 from the sampled formation fluid 146 (and its associated pressure) within the flowline 92 and are transparent to a wavelength range of interest to facilitate optical analysis of the fluid. As will be appreciated, some portion of the electromagnetic radiation 148 is absorbed by the sampled fluid 146, and the extent of such absorption varies for different wavelengths and sampled fluids. The optical density of the fluid 146 at one or more wavelengths may be determined based on data from the spectrometer 104 by comparing the amount of radiation emitted by the emitter 142 and the amount of that radiation received at detector 144. It will be appreciated that the optical density (also referred to as the absorbance) of a fluid at a given wavelength is calculated as the base-ten logarithm of the ratio of electromagnetic radiation incident on the fluid to that transmitted through the fluid for the given wavelength. The spectrometer 104 may include any suitable number of measurement channels for detecting different wavelengths, and may include a filter-array spectrometer or a grating spectrometer. Further, as noted above, the data obtained with the spectrometer 104 can be used to determine optical densities of sampled fluids.

Figure 6:
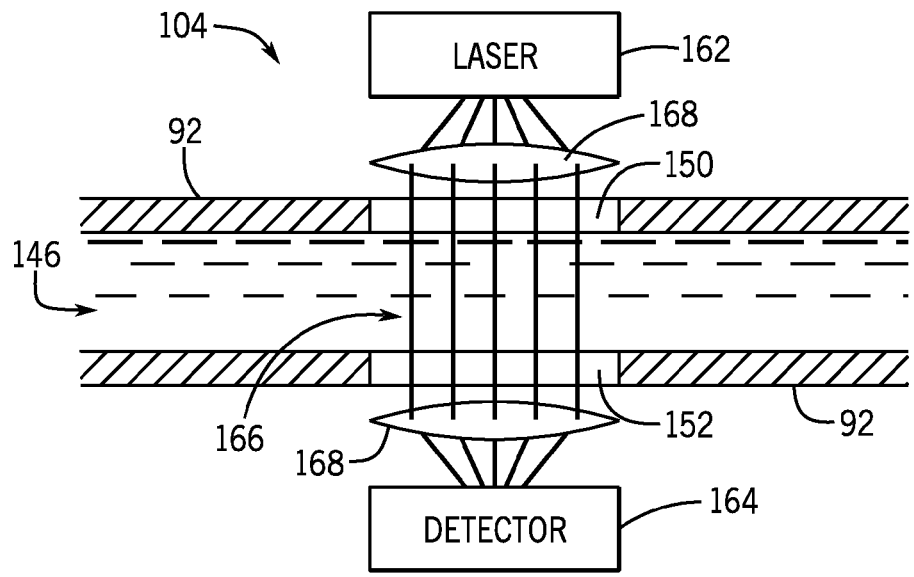
FIG. 6 is an example of a spectrometer having a laser for emitting electromagnetic radiation into a fluid in the flowline in accordance with one embodiment.

By way of example, in one embodiment the spectrometer 104 is provided in the form generally depicted in FIG. 6. In this embodiment, the spectrometer 104 includes a laser 162 that emits electromagnetic radiation 166 into the fluid 146 and a portion of the radiation 166 is received by the detector 164, as generally described above. It will be appreciated that the spectrometer 104 may include other components that are not depicted in FIGS. 5 and 6. For instance, the spectrometer 104 can include an amplifier for boosting detector signals representative of received radiation and an analog-to-digital converter for converting the representative signals for use by a processor (e.g., processor 120 of the controller 100) and for digital storage. The spectrometer 104 can also include lenses 168 to facilitate transmission of the radiation 166 to the detector 164. Additionally, the spectrometer 104 can be used to analyze fluids flowing in the flowline 92 in a high-temperature, high-pressure environment, such as that which may be present downhole in a well.

The laser 162 of the spectrometer 104 can be a quantum cascade laser and, in at least some embodiments, the quantum cascade laser is configured to emit radiation 166 in the mid-IR region of the electromagnetic spectrum and the detector 164 is configured to receive mid-IR radiation. In some other types of semiconductor lasers, electrons recombine with holes across a material bandgap to generate light. In quantum cascade lasers, however, light is generated by electrons jumping between energy levels of quantum wells.

The energy levels in quantum cascade lasers can be controlled by tailoring the quantum well thicknesses, thus enabling design and control of the resulting laser wavelength. Furthermore, multiple stages of quantum wells can be cascaded so that an electron traversing the device can create many laser photons. This enables quantum cascade lasers with continuous wave operation and high output power levels. In at least some embodiments, the quantum cascade laser or other laser 162 of the spectrometer 104 can be tuned over a range of energy levels within the mid-IR spectral region. Such tuning can be performed in any suitable manner through known techniques.

Additionally, the detector 164 could be provided in the form of a quantum cascade detector. In some embodiments, the laser 162 and the detector 164 could both be quantum cascade devices, with each configured to both emit and detect mid-IR radiation. In such instances, either or both of the quantum cascade devices 162 and 164 could emit or receive mid-IR radiation. Such bidirectional operability may provide the system with redundancy and increased reliability. Further, the quantum cascade devices 162 and 164 could be fabricated on the same substrate and, in some instances, could be functionally or structurally identical to one another.

Figure 7:
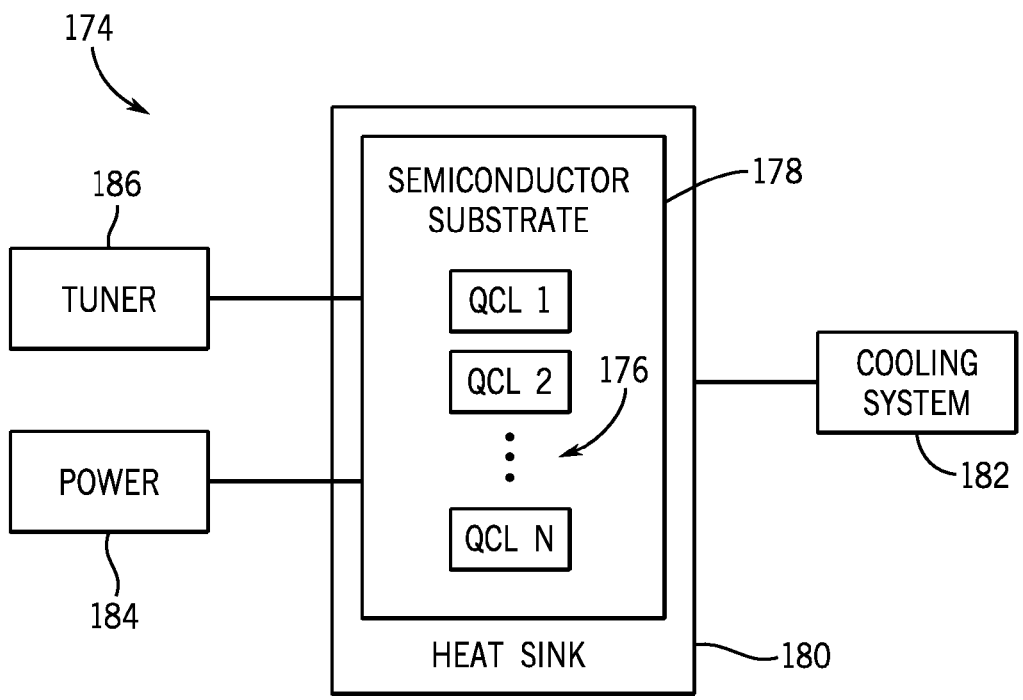
FIG. 7 is a block diagram of an apparatus that can be used in a spectrometer, the apparatus including multiple quantum cascade lasers formed on a semiconductor substrate, in accordance with one embodiment.

One example of an apparatus 174 that could be used in the spectrometer 104 to emit radiation for analysis of a fluid is generally depicted in FIG. 7. In this example, the apparatus 174 includes multiple quantum cascade lasers 176 formed on a semiconductor substrate 178 (e.g., a semiconductor chip or wafer). In at least some embodiments, the multiple quantum cascade lasers 176 are formed monolithically on a shared semiconductor substrate 178 so that a single substrate 178 could be used to emit radiation at multiple wavelengths. When the spectrometer 104 is expected to be used downhole or in other high temperature environments (e.g., up to 200° C.), the apparatus 174 can include any suitable features that facilitate operation of the lasers 176 in such environments. For example, as shown in FIG. 7, the semiconductor substrate 178 can be mounted on a heat sink 180. In some embodiments the heat sink 180 can passively dissipate heat generated by the lasers 176 and the substrate 178; in others, a cooling system 182, such as a refrigeration system, another fluid circulation system, or heat pipes, can be used to facilitate heat dissipation from the lasers 176 and the substrate 178. The apparatus 174 can also include any suitable power source 184 and tuning device 186 for powering and tuning the lasers 176 to desired energy levels.

The number (N) of quantum cascade lasers 176 may vary depending on the tunable range of the lasers 176 and the wavelengths of interest for fluid analysis. At least some species of interest, such as hydrogen sulfide, carbon dioxide, methane, and ethane, have absorption bands or peaks in the mid-IR region, and the wavelengths of interest may correspond to such absorption bands of species of interest in the fluid. For example, wavelengths of interest may include 3.3 microns (for methane), 3.8 microns (for hydrogen sulfide), and 4.26 microns (for carbon dioxide). Although several lasers 176 are depicted in FIG. 7, other embodiments could include just one or two lasers 176. In some embodiments, one or more quantum cascade lasers 176 are configured to emit energy having a wavelength between 3.1 microns and 4.5 microns. In at least one instance, a single quantum cascade laser 176 can be tuned across a range of wavelengths (e.g., from 3.1 to 4.5 microns) to enable analysis of the fluid at multiple wavelengths of interest using that single quantum cascade laser 176. In some embodiments the one or more quantum cascade lasers 176 are configured to emit electromagnetic radiation just in the mid-IR spectral region.

The lasers 176 could be configured to collectively cover a majority of the mid-IR spectral region (e.g., a portion having wavelengths of 3-15 microns) or a smaller portion of the mid-IR region. Further, in some instances, use of the spectrometer 104 with the apparatus 174 may enable real time, in-situ detection of carbon dioxide, hydrogen sulfide, methane, and ethane in downhole fluids with high sensitivity (e.g., sensitivity of hundreds of parts-per-billion, one hundred parts-per-billion, tens of parts-per-billion, ten parts-per-billion, or one part-per-billion for these species).

Figure 8:
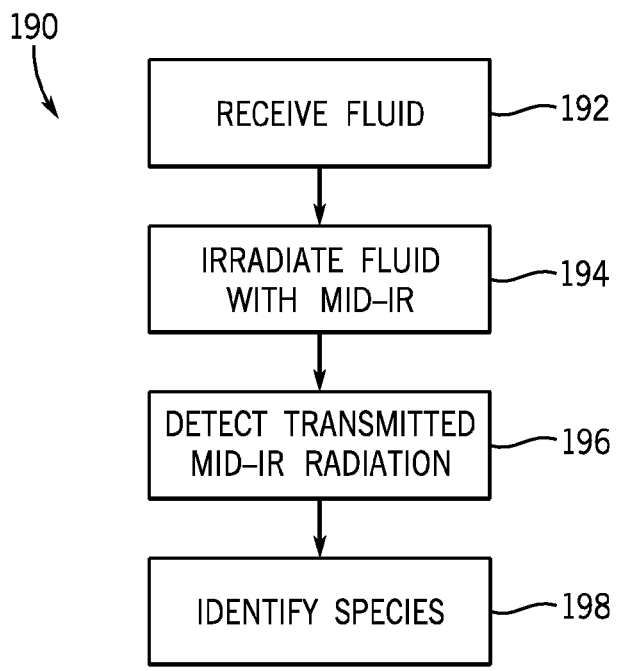
FIG. 8 is a flowchart for identifying species in a sampled fluid using mid-infrared radiation in accordance with one embodiment.

One example of a process for identifying species of interest in a fluid is generally represented by flowchart 190 in FIG. 8. In this embodiment, a sample of the fluid is received (block 192) by a spectrometer (e.g., spectrometer 104). For downhole fluid analysis, a formation fluid may be sampled by a downhole tool, such as with the fluid sampling tool 62 described above. The received fluid is then irradiated (block 194) with electromagnetic radiation in the mid-IR spectral region. In at least some instances, the mid-IR radiation is emitted with one or more quantum cascade lasers, as described above. The wavelengths of the electromagnetic radiation can be selected to correspond to absorption bands of chemical species of interest that may be present in the sampled fluid. In some embodiments, a different quantum cascade laser is used to emit each selected wavelength. In another embodiment, a single quantum cascade laser could be used to emit at one wavelength corresponding to the absorption band of one species of interest and then tuned to emit at a different wavelength corresponding to the absorption band of a different species of interest. Indeed, depending on the range of wavelengths of interest, a single quantum cascade laser could be tuned to cover the entire range (e.g., 3-5 microns).

Some amount of this radiation is transmitted through the fluid and detected (block 196). As discussed above, the irradiation with and detection of the mid-IR radiation can be performed by any of various suitable spectrometers 104. Optical data for the fluid (e.g., optical densities of the fluid at measured wavelengths) can then be used to identify species of interest in the fluid (block 198). Identification of species of interest includes detection of the species of interest, which in at least some embodiments includes determining levels of the species of interest in the fluid (e.g., levels of carbon dioxide, hydrogen sulfide, methane, and ethane in the fluid).

Such species of interest may vary between applications, and the presently disclosed techniques could be used to identify any of a variety of species having absorption bands in the mid-IR spectral region. For downhole fluid analysis, identified species of interest could include hydrogen sulfide, methane, ethane, various other hydrocarbon species, and carbon dioxide. Some downhole tools use spectrometers operating in the visible and SNIR spectral regions and may have certain difficulties in detecting hydrogen sulfide or in distinguishing methane from ethane, as these species have overlapping absorption bands in those spectral regions. In at least some embodiments, however, the use of mid-IR radiation (e.g., from one or more quantum cascade lasers) enables interrogation of a fluid at wavelengths corresponding to absorption bands within the mid-IR spectral region for the species of interest. This may facilitate detection of hydrogen sulfide and distinguishing between methane and ethane in the received fluid based on optical data for wavelengths corresponding to absorption bands of these species.

The use of mid-IR radiation may also facilitate identification of carbon dioxide in a received fluid. Carbon dioxide has a strong absorption mode at 4.26 microns due to the fundamental stretching modes of the C=O bonds of the molecule. Other fluids found downhole, such as water and oils, have absorption at 4.26 microns, but absorption by these other fluids is not as strong as that of carbon dioxide. In some conditions, carbon dioxide can be detected in downhole fluids through spectroscopic analysis in the near-infrared (NIR) wavelength regime. In the NIR regime, carbon dioxide has three weak absorption peaks that are overtones of the fundamental modes. These peaks overlap with a very strong water peak, which (depending on the level of water saturation of the fluid) could mask, distort, and render the carbon dioxide signatures immeasurable.

Figure 9:
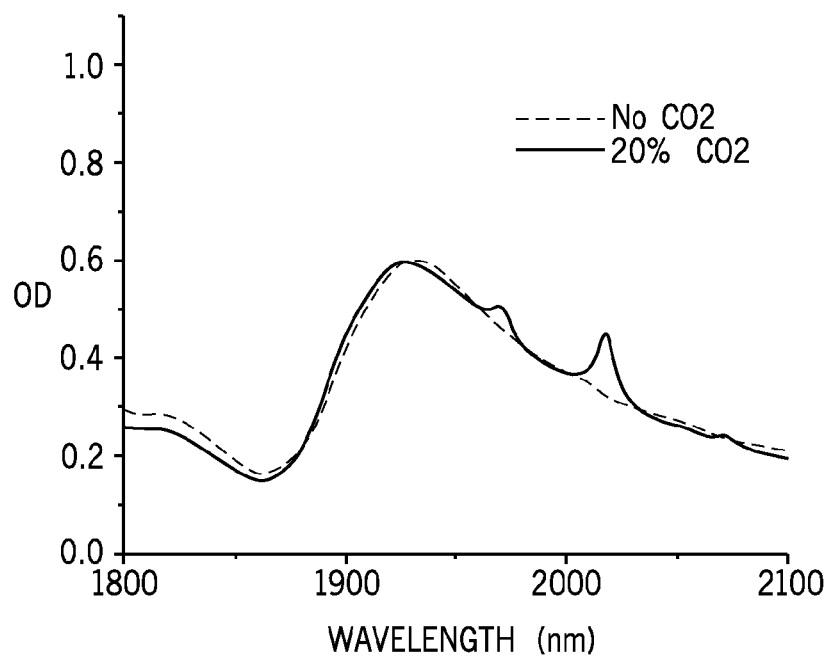
FIGS. 9 and 10 are graphs generally depicting optical densities of certain fluids at wavelengths in the near-infrared and mid-infrared spectral regions.
Figure 10:
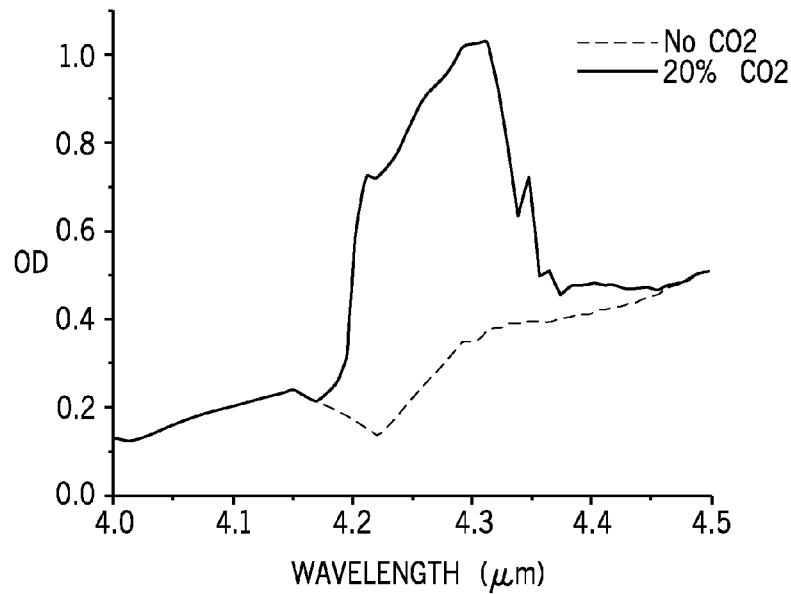

This overlap is generally depicted in FIG. 9, which shows: (1) absorption spectra within a portion of the NIR range for: (1) a fluid sample that is mostly decane with 7.5% water (by volume) and has no carbon dioxide, and (2) the same fluid with 20% carbon dioxide (by volume). In this illustration, the carbon dioxide peaks are distorted by the water peak, and it will be appreciated that the distortion would increase with smaller fractions of carbon dioxide and larger cuts of water. In contrast, the absorption spectra for the same fluid (with and without carbon dioxide) in part of the mid-IR range is shown in FIG. 10, in which the carbon dioxide signature can be readily distinguished from the spectrum for water and oil. In some instances using the NIR region, reliability of carbon dioxide detection may be noticeably impacted at water cuts as low as 2.5% by volume and deemed unreliable at water cuts as low as 7.5% by volume. In some embodiments of the present technique, however, laser spectroscopy with mid-IR radiation is used to determine levels of carbon dioxide in water-saturated fluids, such as those having water contents above 2.5% or 7.5% by volume.

Figure 11:
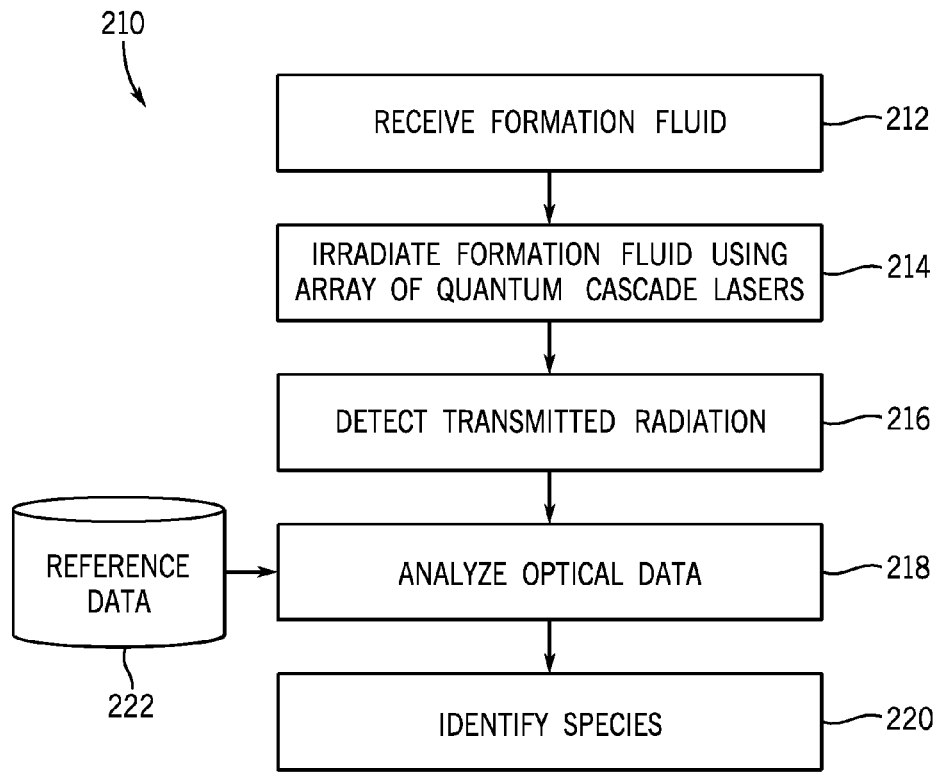
FIG. 11 is a flowchart for identifying species in a sampled formation fluid using multiple quantum cascade lasers for spectroscopic analysis in accordance with one embodiment.

Another example of a process for detecting species in an analyzed fluid is represented by flowchart 210 in FIG. 11. In this example, a formation fluid is received (block 212) in a downhole tool having a spectrometer, such as one of those described above. The received formation fluid is then irradiated (block 214) with electromagnetic radiation (e.g., mid-IR radiation) from an array of quantum cascade lasers, and radiation transmitted through the formation fluid is detected (block 216). In contrast to some other mid-IR sources, quantum cascade lasers may have smaller emission areas and may produce higher power levels in high-temperature environments (e.g., above 100° C.). When used in a downhole spectrometer, this may facilitate detection of radiation transmitted through the formation fluid. The optical data measured from the spectrometer is then analyzed (block 218) to determine optical properties of the fluid (e.g., absorbance) and to identify species in the fluid (block 220) using the determined optical properties. Reference data 222, such as stored absorbance data for individual species at wavelengths of interest, can be used to facilitate real time analysis of the measured optical data and identification of species in the analyzed formation fluid. As previously noted, the analysis of optical data and identification of species could be performed by the controller 100 or another suitable processor-based system.

While certain examples of the spectrometer 104 are described above in the context of a downhole tool, it is noted that the spectrometer 104 could be used independent of a downhole tool. For instance, the spectrometer 104 and the presently disclosed techniques could be used at the surface to analyze fluids produced from a well. Further, the spectrometer 104 and the presently disclosed techniques could be used in other applications, such as medical diagnostics, industrial process control, climate and pollution monitoring, for various purposes (e.g., trace bio-marker sensing and detecting pollutants and chemicals with high selectivity and sensitivity). Species of interest in these other fields may include carbon dioxide, methane, ammonia, water vapor, and organic species, to name but several examples. Additionally, in one embodiment photo-acoustic spectroscopy could also or instead be used to study a formation fluid or some other fluid. A photo-acoustic spectrometer could include at least one laser (e.g., quantum cascade lasers 176) and microphone. The fluid could be illuminated with the laser output so that absorbed light locally heats the fluid sample. This heating would create a pressure wave, which could be measured by the microphone.

The foregoing outlines features of several embodiments so that those skilled in the art may better understand aspects of the present disclosure. Those skilled in the art should appreciate that they may readily use the present disclosure as a basis for designing or modifying other processes and structures for carrying out the same purposes or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

The invention claimed is:

1. A method comprising:
   sampling formation fluid within a well; and
   determining formation fluid properties for the sampled formation fluid through downhole fluid analysis, wherein determining formation fluid properties for the sampled formation fluid includes:
   using a spectrometer having a plurality of quantum cascade lasers to determine optical properties of the formation fluid; and
   determining levels of multiple chemical species in the formation fluid using the determined optical properties of the formation fluid; and
   wherein the formation fluid has a water content above 2.5% by volume, and determining levels of multiple chemical species in the formation fluid includes determining a level of carbon dioxide in the formation fluid having the water content above 2.5% by volume.

2. The method of claim 1, wherein determining levels of multiple chemical species in the formation fluid includes determining levels of carbon dioxide and hydrogen sulfide in the formation fluid.

3. The method of claim 1, wherein determining levels of multiple chemical species in the formation fluid includes determining levels of methane and ethane in the formation fluid.

4. The method of claim 1, wherein sampling formation fluid within the well includes receiving the formation fluid within a downhole tool having the spectrometer, and the downhole tool is configured to determine the levels of multiple chemical species in the formation fluid using the determined optical properties of the formation fluid.

5. The method of claim 1, wherein the spectrometer is configured to emit electromagnetic radiation in just the mid-infrared portion of the electromagnetic spectrum.

6. The method of claim 1, wherein determining levels of multiple chemical species in the formation fluid using the determined optical properties of the formation fluid includes determining levels of each of carbon dioxide, hydrogen sulfide, methane, and ethane in the formation fluid using optical data indicative of absorption bands of the carbon dioxide, hydrogen sulfide, methane, and ethane within the mid-infrared portion of the electromagnetic spectrum.

7. The method of claim 1 wherein the water content of the formation fluid is above 7.5% by volume, and determining levels of multiple chemical species in the formation fluid includes determining the level of carbon dioxide in the formation fluid having the water content above 7.5% by volume.

8. The method of claim 1, comprising using one quantum cascade laser of the plurality of quantum cascade lasers to irradiate the formation fluid with radiation having a first wavelength corresponding to an absorption band of one chemical species of interest and then tuning the one quantum cascade laser to irradiate the formation fluid with radiation having a second wavelength corresponding to an absorption band of another chemical species of interest.

* * * * *